US00PP08357P

United States Patent [19]

Bull

[11] Patent Number: Plant 8,357

[45] Date of Patent: Aug. 31, 1993

[54] IMPATIENS PLANT NAMED INGE

[76] Inventor: Norbert Bull, Gärtnersiedlung 2, 2351 Gönnebek, Fed. Rep. of Germany

[21] Appl. No.: 802,861

[22] Filed: Dec. 6, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

An Impatiens plant named Inge characterized by its bicolored flowers comprised of a coral red base color ane a more pinkish coral overlay, compact growth habit, medium, dark green non-variegated foliage, medium early flowering, and its floriferous habit.

2 Drawing Sheets

1

The present invention relates to a new and distinctive cultivar of Impatiens plant, botanically known as Impatiens, and referred to be the cultivar name Inge. The new cultivar was developed by me through controlled breeding by crossing seed of female parent identified as Seedling No. 18 with male or pollen parent identified as Seedling No. 14. Both parents are unreleased and propriety lines.

Asexual reproduction of the new cultivar by the inventor by terminal or stem cuttings taken at Gönnebek, Federal Republic of Germany has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Bicolored flower petals having a base color of avid red infused with a lighter coral pink.
2. Compact growth habit.
3. Relatively small, dark green foliage.
4. Very floriferous habit.
5. Medium early flowering.
6. Suitable for pot plant, patio, bedding plant or hanging basket culture.

Inge has a main flower color similar to the flower color of the cultivar Sesia. However, Inge is bicolored, having a coral pink painting or overlay. Inge also has a more compact growth habit and non-variegated foliage.

The accompanying colored photographs illustrate the overall appearance of this cultivar, showing the colors as true as it is reasonably possible to obtain in a colored reproduction of this type. The photo at the top of sheet 1 comprises a top perspective view of a potted plant of Inge. The bottom photo on sheet 1 shows a single flower (top side), and top and bottom views of a typical leaf.

The photograph on sheet 2 shows the upper side and under side of typical flowers, a bud with attached spur, and the upper side and bottom side of typical leaves. Scales in centimeters are included to show the size of these parts. The flower and foliage colors in the third photograph do not accurately depict true color, and reference should be made to the photos on sheet 1 and the described color values.

The following is a detailed description of my new Impatiens cultivar based on plants produced under normal commercial practice at Gönnebek, Federal Republic of Germany.

2

Color references are made to The Royal Horticultural Society (R.H.S.) Colour Chart except wher general terms of ordinary dictionary significance are used.

Parentage: Controlled cross between Bull Unnamed Seedling No. 18×Bull Unnamed Seedling No. 14.

Propagation:

*Type cutting.*—Stem 15–20 mm long will grow to 4–5 cm in 21 days.

*Time to initiate roots.*—8 days at 22° C. summer.

*Time to initiate roots.*—10 days at 20° C. winter.

*Rooting habit*—Heavy and rapid.

Plant description:

*Form.*—Symmetrically mounded, self-branching.

*Habit of growth.*—Compact growth habit. Eight (8) weeks after sticking stem cuttings in 12 cm pots, plant is approximately 30 cm in diameter and 30 cm in height, measured from top of pot.

Foliage description:

(1) *Size.*—Relatively small length approximately 9–10 cm; width 3–4 cm at point of maximum width.

(2) *Shape.*—Generally ovate, with acute to acuminate tip and rounded to acute base; see photos.

(3) *Margin.*—Midly serrated.

(4) *Color.*—(a) Young foliage upper surface: Dark green, approximately R.H.S. 139A. (b) Under surface: Dark greyed-purple. (c) Mature foliage upper surface: Dark green, approximately R.H.S. 139A. (d) Under surface: Dark greyed-purple, approximately 184B.

(5) *Veination.*—Red veins on under side (see photo).

(6) *Variegation.*—None.

Flowering description:

*Flowering habit.*—Flowers from leaf whorl in uniform manner.

*Natural flowering season.*—March until October.

*Flower buds.*—Typical; pink red in color.

*Flowers borne.*—On Pedicels red-purple in color.

*Quantity of flowers.*—Very floriferous. Flowers both mask the crown and occur above the leaf canopy.

*Spur.*—Downwardly curved from base of calyx, approximately 4–5 cm in length and red-purple in color.

*Longevity.*—Flowers are long lasting and non-fading.

Petals:

*Number of petals.*—Five (5).

*Shape.*—Generally heart-shaped (see photo).

*Color.*—Upper surface: Main color 39A painted or overlayed with 48C to give bicolor effect. Under surface: Slightly lighter than 39A.

*Size of flower.*—Medium, approximately 5.5 cm. in diameter.

Reproductive organs:

*Stamens.*—Five (5)

*Anthers.*—Hooded, orange-yellow color.

*Pollen color.*—White.

*Stigma.*—Five in number, red in color.

*Styles.*—Red in color.

*Ovary.*—5 in number, size 3-5 mm., green-brown in color.

Disease resistance: No disease problems noted to date.

I claim:

1. A new and distinct Impatiens plant named Inge, as illustrated and described.

* * * * *

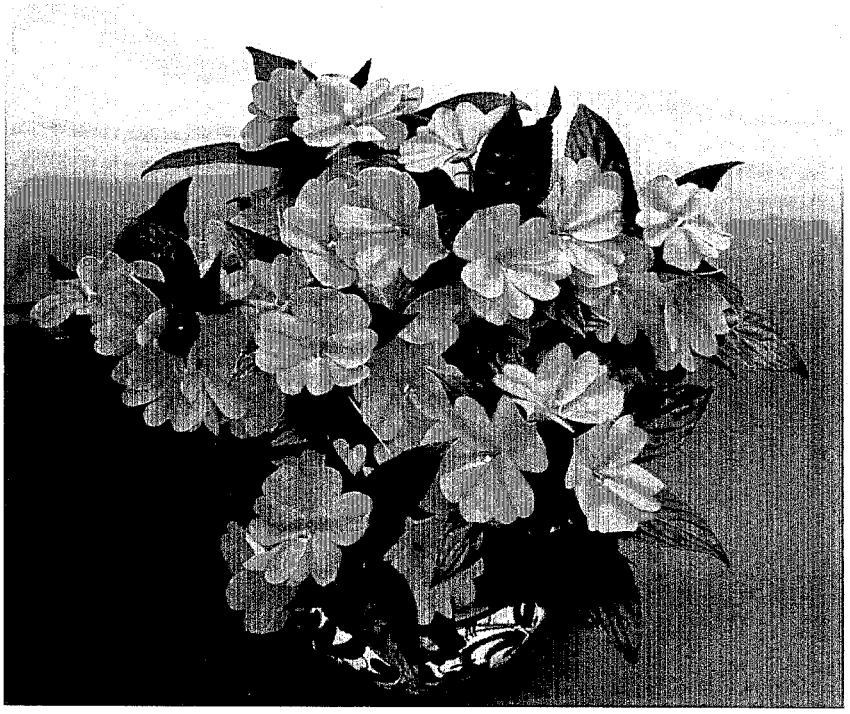
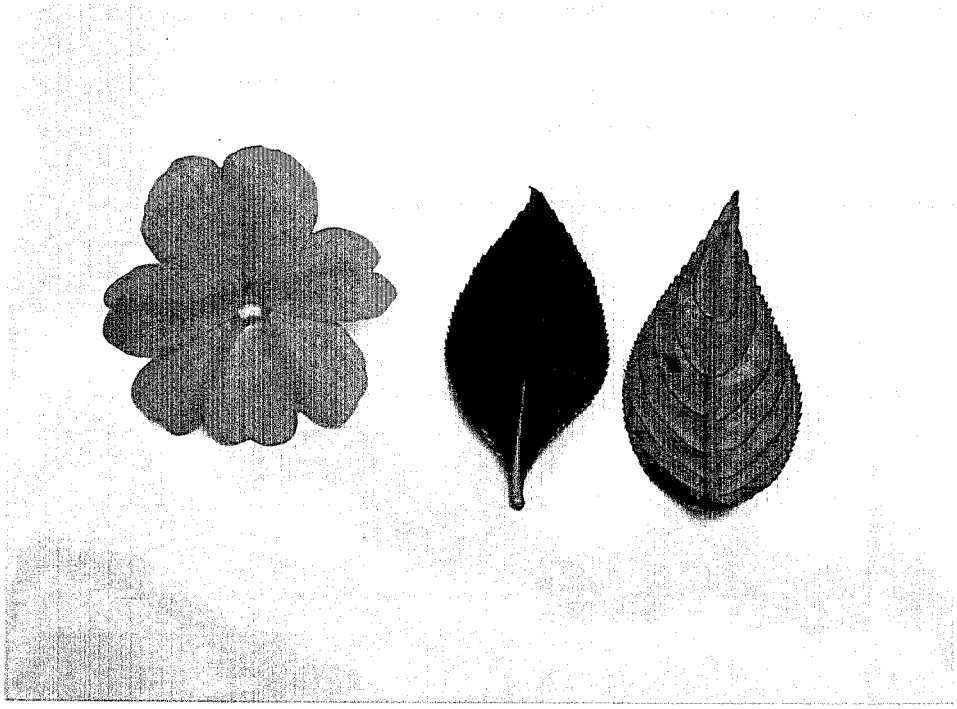

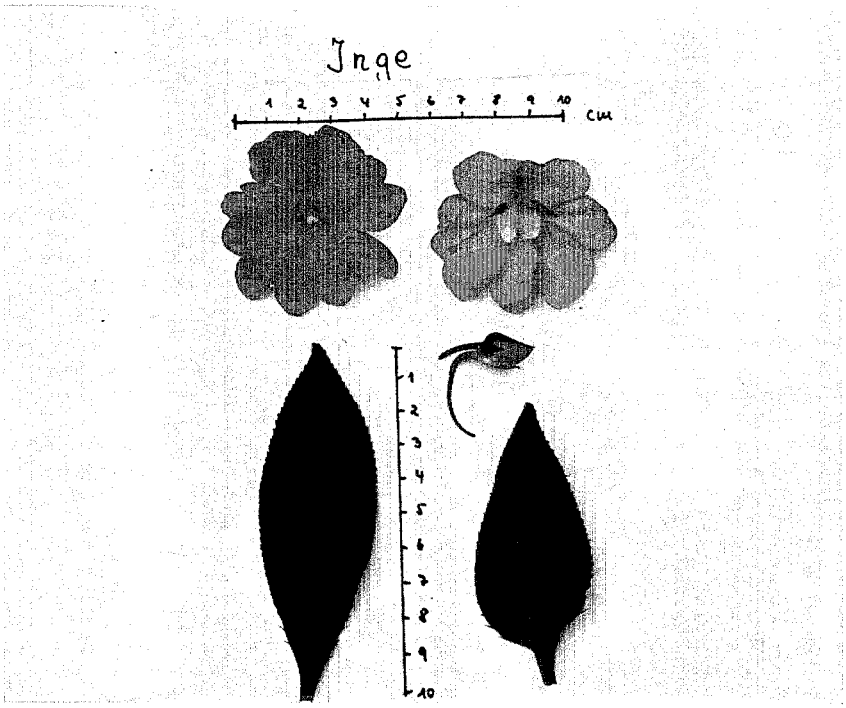
Inge
1 2 3 4 5 6 7 8 9 10 cm
1
2
3
4
5
6
7
8
9
10